United States Patent
Bass

(10) Patent No.: US 7,588,537 B2
(45) Date of Patent: Sep. 15, 2009

(54) CONNECTOR WITH SAFETY LATCH FOR A SURGICAL RETRACTOR

(75) Inventor: Daniel Bass, El Granada, CA (US)

(73) Assignee: West Coast Surgical, LLC., El Granada, CA (US)

( * ) Notice: Subject to any disclaimer, the term of this patent is extended or adjusted under 35 U.S.C. 154(b) by 330 days.

(21) Appl. No.: 11/541,698

(22) Filed: Oct. 3, 2006

(65) Prior Publication Data

US 2007/0055110 A1    Mar. 8, 2007

Related U.S. Application Data

(63) Continuation-in-part of application No. 11/219,847, filed on Sep. 7, 2005.

(51) Int. Cl.
*A61B 1/32* (2006.01)

(52) U.S. Cl. .............. 600/234; 600/210; 600/211; 600/228; 600/235; 600/244

(58) Field of Classification Search ............... 600/234, 600/235, 201, 210, 211, 228, 244
See application file for complete search history.

(56) References Cited

U.S. PATENT DOCUMENTS

| | | |
|---|---|---|
| 768,069 A | 8/1904 | O'Brien |
| 1,576,352 A | 3/1926 | Nordling |
| 3,003,214 A | 10/1961 | Geraghty |
| 3,405,966 A | 10/1968 | Harley |
| 3,405,967 A * | 10/1968 | Harley ............. 294/82.33 |
| 4,263,899 A | 4/1981 | Burgin |
| 4,379,579 A | 4/1983 | Mahan et al. |
| 4,544,324 A | 10/1985 | Hornung |
| 4,613,180 A | 9/1986 | Pope |
| 5,512,038 A | 4/1996 | O'Neal et al. |
| 5,813,978 A | 9/1998 | Jako |
| 5,893,831 A | 4/1999 | Koros et al. |
| 5,902,233 A | 5/1999 | Farley et al. |
| 5,931,777 A | 8/1999 | Sava |
| 5,993,385 A | 11/1999 | Johnston et al. |
| 6,042,540 A | 3/2000 | Johnston et al. |
| 6,206,828 B1 | 3/2001 | Wright |
| 6,305,868 B1 | 10/2001 | Kinoshita et al. |
| 6,324,732 B1 | 12/2001 | Arisaka et al. |
| 6,572,540 B2 | 6/2003 | Dobrovolny |
| 6,663,562 B2 | 12/2003 | Chang |
| 6,733,444 B2 | 5/2004 | Phillips |
| 6,736,775 B2 | 5/2004 | Phillips |
| 6,887,197 B2 | 5/2005 | Phillips |
| 6,898,829 B2 | 5/2005 | Loe et al. |
| 2003/0149341 A1 | 8/2003 | Clifton |
| 2004/0049101 A1 | 3/2004 | Phillips et al. |
| 2005/0020885 A1 | 1/2005 | Rein et al. |
| 2006/0178566 A1* | 8/2006 | Fetzer ................ 600/234 |

* cited by examiner

FOREIGN PATENT DOCUMENTS

DE    10254006    3/2004

*Primary Examiner*—Eduardo C Robert
*Assistant Examiner*—Christina Negrelli
(74) *Attorney, Agent, or Firm*—Terry W. Kramer; Kramer & Amado, P.C.

(57) ABSTRACT

A connector for a surgical retractor is shown. The connector includes a body member having an opening for receiving a nipple of a retractor blade. The connector also includes a retainer pivotally attached to the body member between an open position and a closed position. A lock mechanism locks the retainer in the closed position so that the nipple of the retractor blade is locked in the connector. A safety latch constrains the lock mechanism when the retainer is in the closed position.

12 Claims, 8 Drawing Sheets

CONNECTOR WITH SAFETY LATCH FOR A SURGICAL RETRACTOR

CROSS-REFERENCE TO RELATED APPLICATIONS

This application is a continuation-in-part of application Ser. No. 11/219,847 filed Sep. 7, 2005.

BACKGROUND

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades can be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

For interchangeable retractor blades, there are several connector designs for allowing the retractor blades to be interchangeably attached to the retractor body. One connector is the top-loading ball snap design, which resembles the mechanism found in common ball-and-socket wrench kits.

The ball snap design uses a top-loading socket which fits over the top of the ball snap. The retractor blades used with the ball snap design typically have a top end bent at a right angle to create a perpendicular section on which the ball snap is mounted.

The ball snap design allows the retractor blades to positively lock into the top-loading socket. This allows the entire retractor to be assembled and handed to the surgeon without the risk of the retractor blades falling off. It also permits the entire retractor to be repositioned in the incision without the risk of the retractor blades becoming detached from the retractor body.

However, many surgeons prefer to position the retractor blades first before attaching the retractor body. Positioning the retractor blades first makes it much easier for the surgeon to create a precise surgical exposure before attaching the retractor body. Pre-positioning of the retractor blades also facilitates the selection of the proper retractor blade length and width.

With the ball snap design, the surgeon must line up the sockets in the retractor body over the tops of the ball snaps before snapping the retractor blades in place. This is a difficult process, as the retractor body arms must be aligned over the ball snaps precisely in order to attach the retractor blades. This alignment process is complicated by the hinged arms and ratcheting mechanisms often found in retractor bodies.

Current side-loading designs attempt to address these problems by making it easier to load the retractor blades into the retractor body after the surgeon has pre-positioned the retractor blades. Current side-loading designs use a post or rail that allow the retractor blades to be loaded from the side. This allows the retractor body to be placed between the retractor blades and then simply opened up to engage the retractor blades from the side.

However, current side-loading designs do not allow the retractor blades to be positively locked into the retractor body. This means the entire retractor cannot be assembled and then handed to a surgeon without the risk of the retractor blades falling off. The retractor blades are held in place only by the opposing force of the retracted tissue and may become detached from the retractor body if the surgeon tries to reposition the retractor blades inside the incision. Furthermore, current side-loading designs often misalign, resulting in a poor connection between the retractor blade and the retractor body.

What is needed is a surgical retractor with interchangeable retractor blades, where the retractor body can accept the retractor blades easily without the need for precise alignment and where the retractor blades can be positively locked into the retractor body.

SUMMARY

According to an embodiment, a connector includes a body member having an opening for receiving a nipple of a retractor blade. The connector also includes a retainer pivotally attached to the body member between an open position and a closed position. A lock mechanism locks the retainer in the closed position so that the nipple of the retractor blade is locked in the connector. A safety latch constrains the lock mechanism when the retainer is in the closed position.

BRIEF DESCRIPTION OF THE DRAWINGS

Examples of the invention are illustrated, without limitation, in the accompanying figures in which like numeral references refer to like elements and wherein.

DETAILED DESCRIPTION

Figure 1A:
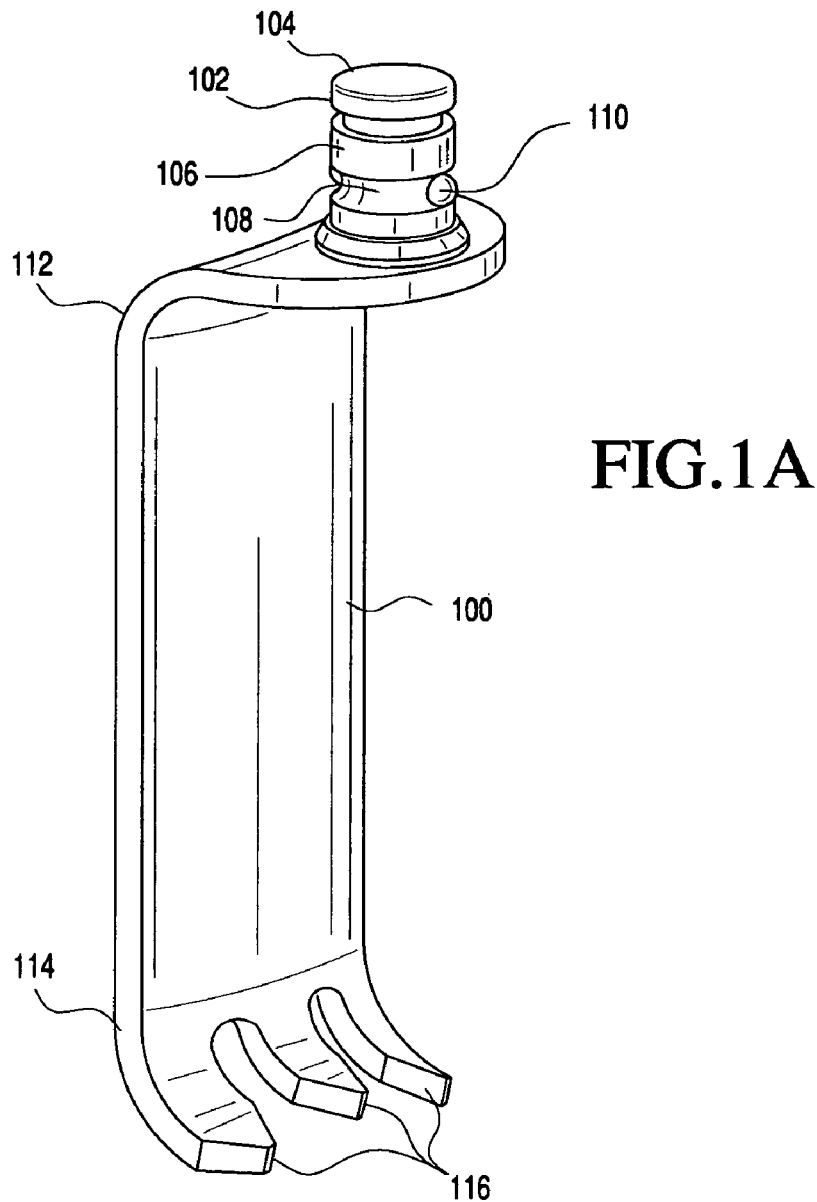
FIGS. 1A, 1B and 1C show perspective diagrams of a surgical retractor blade for use with a connector in with an embodiment of the invention.

For simplicity and illustrative purposes, the principles are shown by way of examples of systems and methods described. In the following description, numerous specific details are set forth in order to provide a thorough understanding of the examples. It will be apparent however, to one of ordinary skill in the art, that the examples may be practiced without limitation to these specific details. In other instances, well known methods and structures are not described in detail so as not to unnecessarily obscure understanding of the examples.

In an example, a connector for a surgical retractor includes a body member, a retainer and a lock mechanism. The body member includes an opening for receiving a nipple of a retractor blade. The retainer is pivotally attached to the body member between an open position and a closed position. The nipple of the retractor blade, when placed into the opening of the body member, engages a mating portion of the retainer and causes the retainer to pivot from the open position to the closed position. The lock mechanism maintains the retainer in the closed position when the nipple is fully inserted into the opening of the body member. Once fully inserted, the nipple may only be removed by disengaging the locking mechanism. In one example, the connector includes a spring to bias the retainer in an open position. In this case, when disengaging the locking mechanism, the retainer ejects, or helps to eject, the nipple from the opening of the body member.

In one example, the opening of the connector is approximately semi-annular in shape and adapted to receive a generally cylindrical nipple. Correspondingly, the mating portion of the retainer is semi-annular and cylindrical. The opening may also include a ridge for aligning with an annular trench located around the periphery of the nipple.

In another example, the opening of the connector is approximately semi-annular in shape and adapted to receive a tapered nipple. Correspondingly, the mating portion of the retainer is semi-annular and tapered. The opening may also include a ridge for aligning with an annular trench located around the periphery of the nipple.

In yet another example, the lock mechanism may include a push button having a base and a shoulder. The base of the push button may reside or partially reside within the retainer while the shoulder is spring biased towards the body member. As the retainer pivots, the shoulder of the push button rides along a slot until the retainer is fully closed. At that point, the shoulder of the push button engages, or pushes into, a recessed notch within the body member. This positively locks the retainer in the closed position until a user disengages the locking mechanism by pushing the push button.

In yet another example, the lock mechanism may include a pawl pivotally attached to the body member between a release position and a lock position. A distal end of the retainer is shaped to mate with the pawl such that the pawl retains the retainer in the closed position. The pawl is spring biased into a lock position but remains in a release position until the retainer is in the closed position.

Figures 1B, 1C:
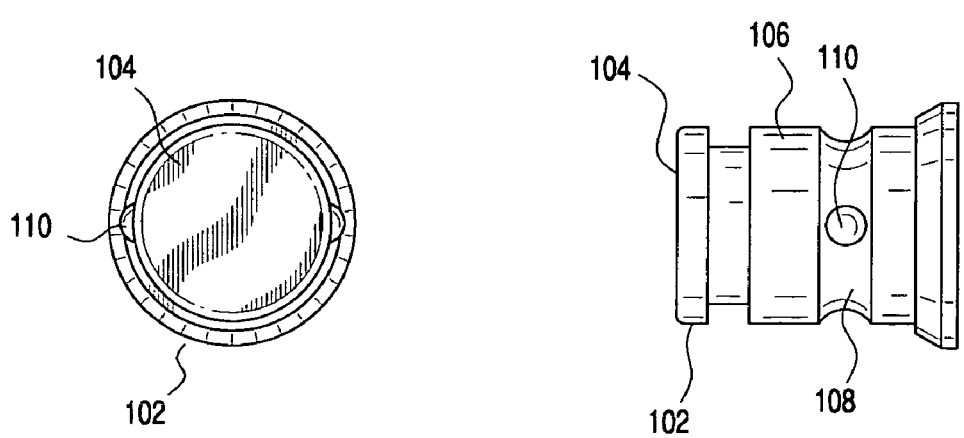

With reference first to FIGS. 1A, 1B and 1C, there is shown a surgical retractor blade 100 including a nipple 102. The nipple 102 is generally cylindrical, with a top surface 104 and a side surface 106. The top surface 104 may have rounded edges to facilitate loading of the retractor blade 100. The side surface 106 may contain a groove 108. The groove 108 may be circumferential around the nipple 102. The nipple 102 may also have a fixing pin 110.

The retractor blade 100 may be rectangular or trapezoidal in shape and may be flat or curved. The retractor blade 100 may also be configured at a right angle rear a proximal end 112 wherein the nipple 102 is attached. The retractor blade 100 has a distal end 114 that may be angled to allow it to reach around and pull back soft tissue. The retractor blade 100 may also contain one or more prongs 116 at its distal end. The prongs 116 may be of different shapes and sizes depending on the application.

The retractor blade 100 may be constructed of plastic, ceramic, aluminum, stainless steel or titanium. A set of retractor blades may also be color-coded with an anodized finish for quick selection of the desired size and length.

Figure 2A:
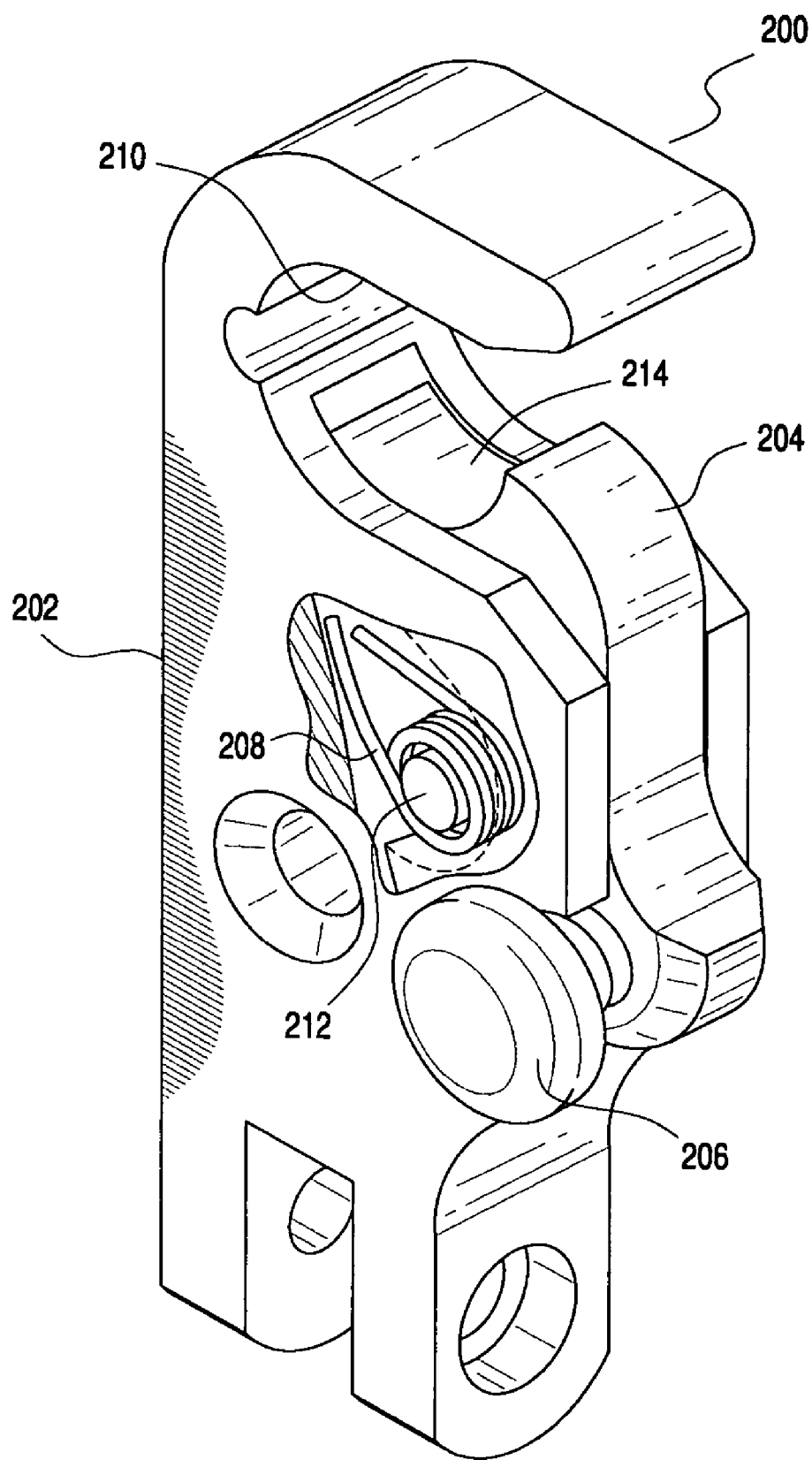
FIGS. 2A, 2B, and 2C show perspective and cut away diagrams of a connector in accordance with an embodiment of the invention.
Figure 5:
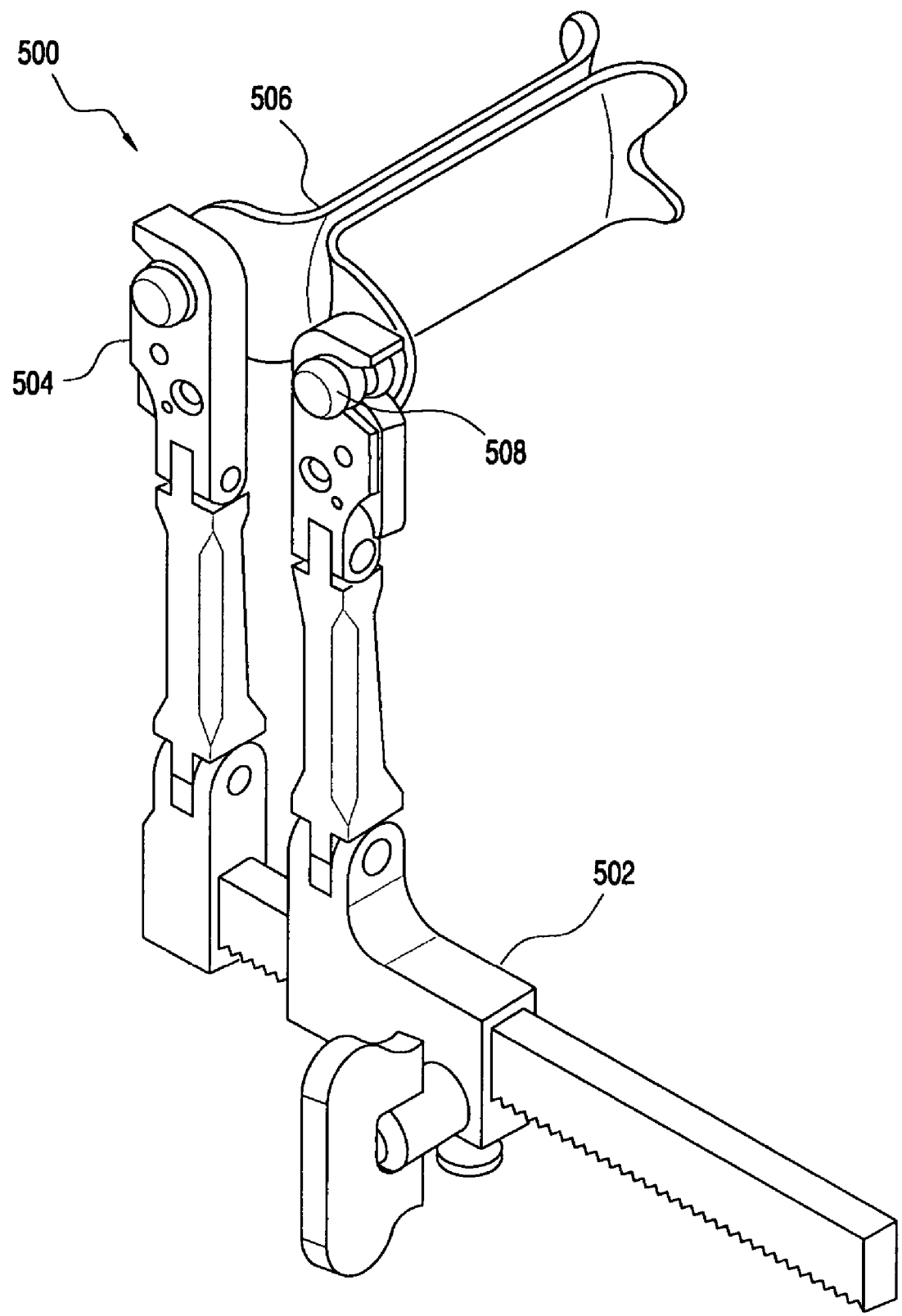
FIG. 5 shows a perspective view of a surgical retractor including connectors in accordance with an embodiment of the invention.

FIG. 2A shows a perspective view of a connector 200 for a surgical retractor (shown in FIG. 5). The connector 200 includes a body member 202, a retainer 204, a lock mechanism 206 and a spring 208. The body member 202 includes an opening 210 for receiving a nipple of a retractor blade such as the one described in FIG. 1. However, the opening 210 may be adapted to receive various types of retractor blades having various types of nipples or connector heads. The retainer 204 is pivotally mounted to the body member 202 at a pivot point and pivots between an open position and a closed position. FIG. 2A shows the retainer 204 in the closed position. The spring 208 biases the retainer 204 in the open position. The biasing provides a force which allows the retainer 204 to eject the nipple from the opening 210 of the body member 202.

The opening 210 of the body member 202 is approximately semi-annular in shape and adapted to receive a generally cylindrical nipple. Correspondingly, a mating portion 214 of the retainer is semi-annular and cylindrical. The opening 202 may also include a ridge 216 (shown in FIG. 2B) for aligning with an annular trench located around the periphery of the nipple.

Figure 2B:
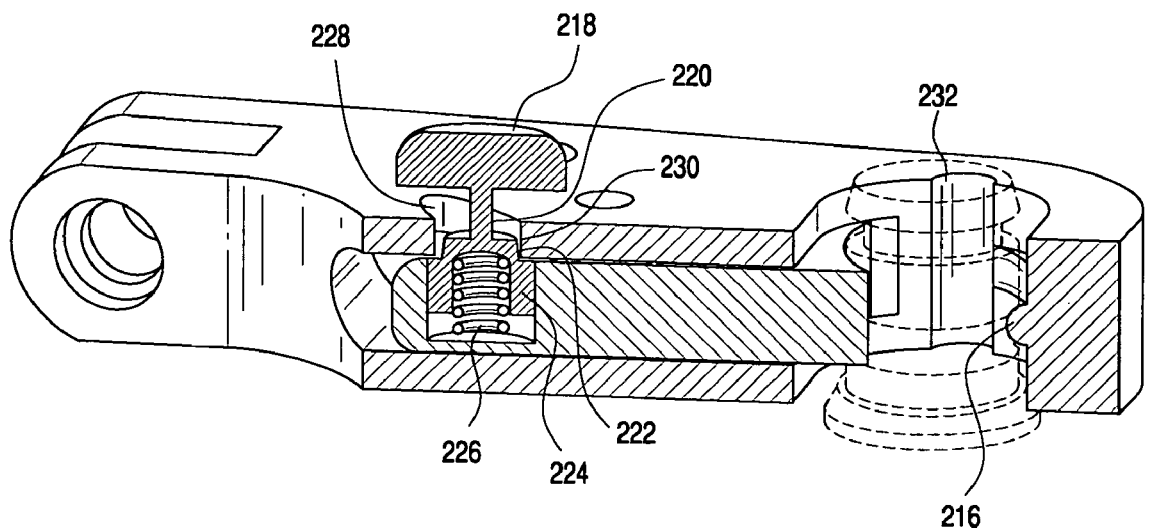

FIG. 2B shows a cut away diagram of the connector 200 of FIG. 2A. As shown in FIG. 2B, the locking mechanism 206 includes a push button 218, a post 220, a shoulder 222, a base 224 and a spring 226. The body member 202 includes a slot 228 and a recessed notch 230. The base 224 and spring 226 are partially mounted in the retainer 204. The spring 226 biases the shoulder 222 against a surface of the body member 202 while the post 220 lies in the slot 228. When the retainer 204 is in the closed position, the shoulder 222 slides into the recess 230 and locks the retainer 204 in the closed position. Pushing the push button 218 moves the shoulder 222 out of the recess 230 and allows the retainer 204 to move to the open position. FIG. 2B also illustrates a notch 232 for mating with a fixing pin of the nipple in order to prevent axial rotation of the retractor blade.

Figure 2C:
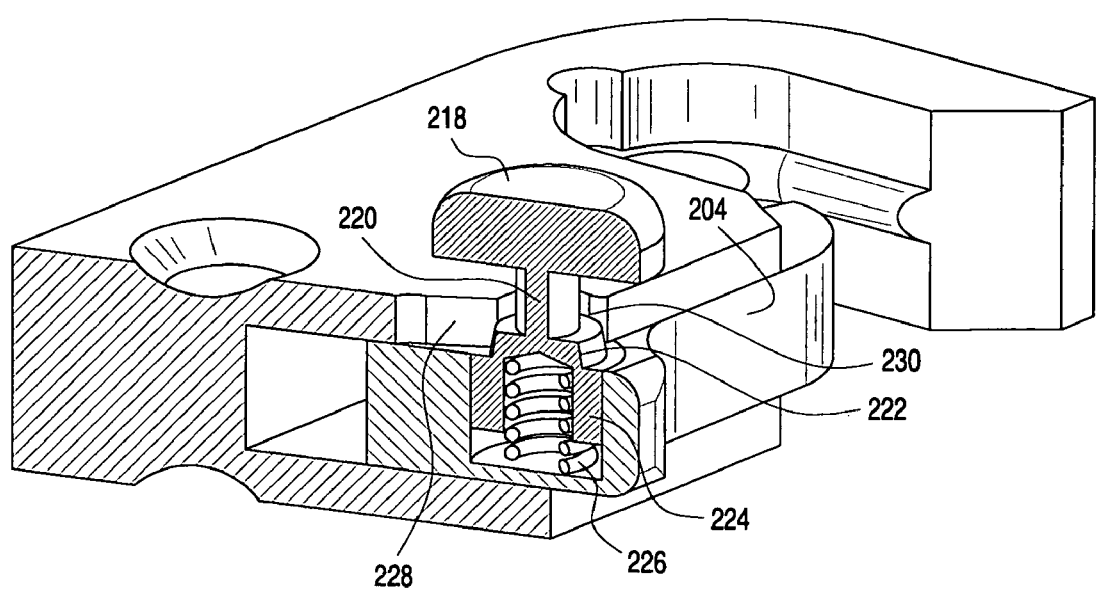

FIG. 2C shows another cut away diagram of the connector 200 of FIG. 2A. As shown in FIG. 2C, the retractor 204 is in the closed position. The spring 226 has forced the shoulder 222 of the locking mechanism 206 into the notch 230. When a user pushes the push button 218 and overcomes the force of the spring 226, the shoulder 222 leaves the notch 230 and the post 220 is able to slide along the slot 228 thus allowing the retainer 204 to move from the closed position to the open position. The spring 208 applies force to the retainer 204 ejecting the nipple from the opening 210 of the body member 202.

Figure 3A:
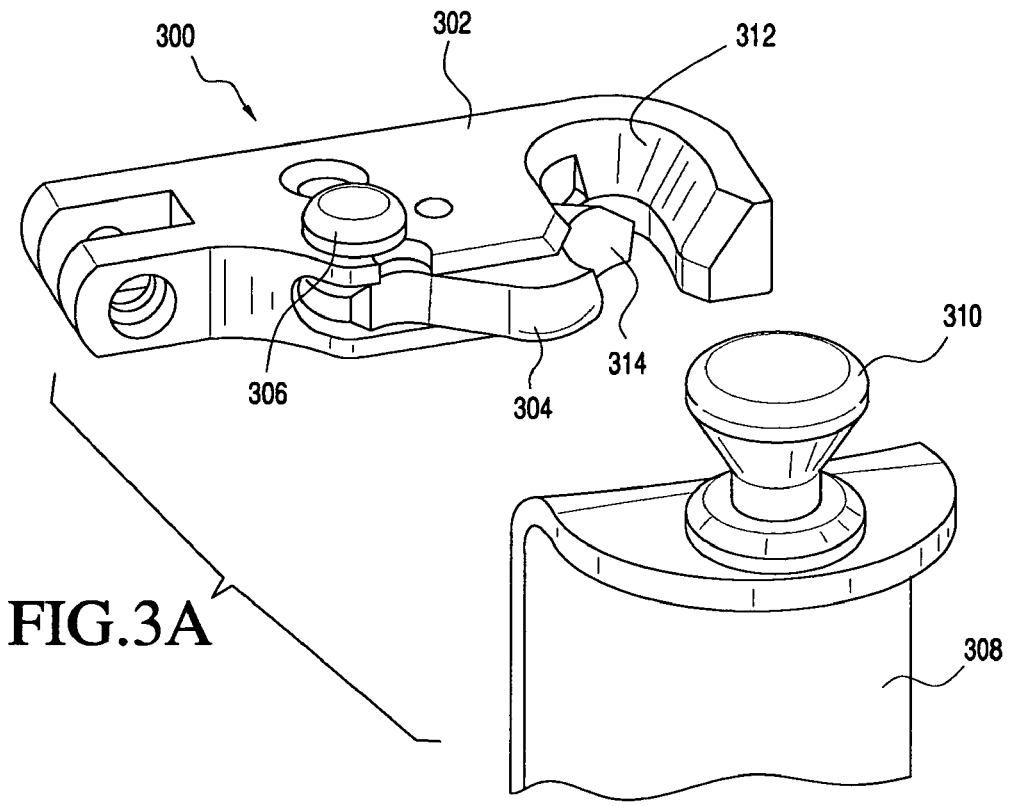
FIGS. 3A and 3B show perspective and cut away diagrams of a connector in accordance with another embodiment of the invention.

FIG. 3A shows a perspective view of a connector 300 for a surgical retractor (shown in FIG. 5). The connector 300 includes a body member 302, a retainer 304, a lock mechanism 306. Also shown in FIG. 3A is a retractor blade 308 having a tapered nipple 310. The body member 302 includes an opening 312 for receiving the nipple 310 of the retractor blade 308. The retainer 304 is pivotally mounted to the body member 302 at a pivot point and pivots between an open position and a closed position. FIG. 3A shows the retainer 304 in the open position.

The opening 312 of the body member 302 is approximately semi-annular in shape and adapted to receive the tapered nipple 310. Correspondingly, a mating portion 314 of the retainer is semi-annular and tapered.

Figure 3B:
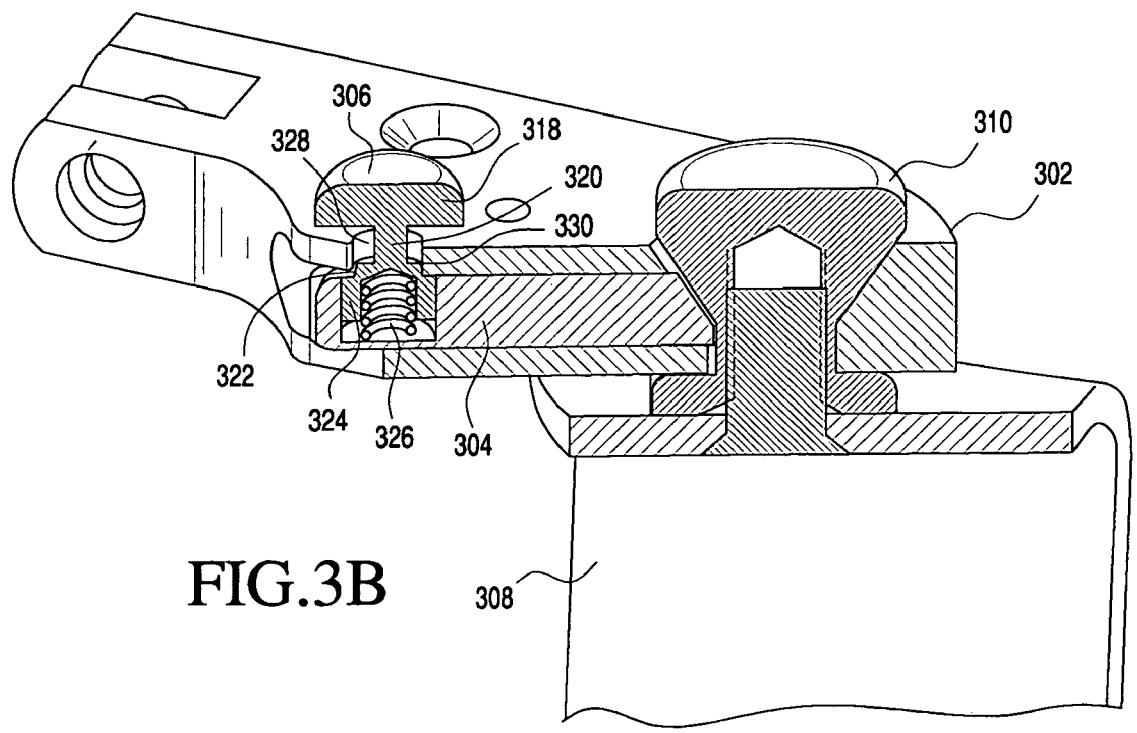

FIG. 3B shows a cut away diagram of the connector 300 of FIG. 3A with the retainer 304 in the closed position retaining the nipple 310 therein. As shown in FIG. 3B, the locking mechanism 306 includes a push button 318, a post 320, a shoulder 322, a base 324 and a spring 326. The body member 302 includes a slot 328 and a recessed notch 330. The base 324 and spring 326 are partially mounted in the retainer 304. The spring 326 biases the shoulder 322 against a surface of the body member 302 while the post 320 lies in the slot 328. When the retainer 304 is in the closed position, the shoulder 322 slides into the recess 330 and locks the retainer 304 in the closed position. Pushing the push button 318 moves the shoulder 322 out of the recess 330 and allows the retainer 304 to move to the open position illustrated in FIG. 3A.

Figure 4A:
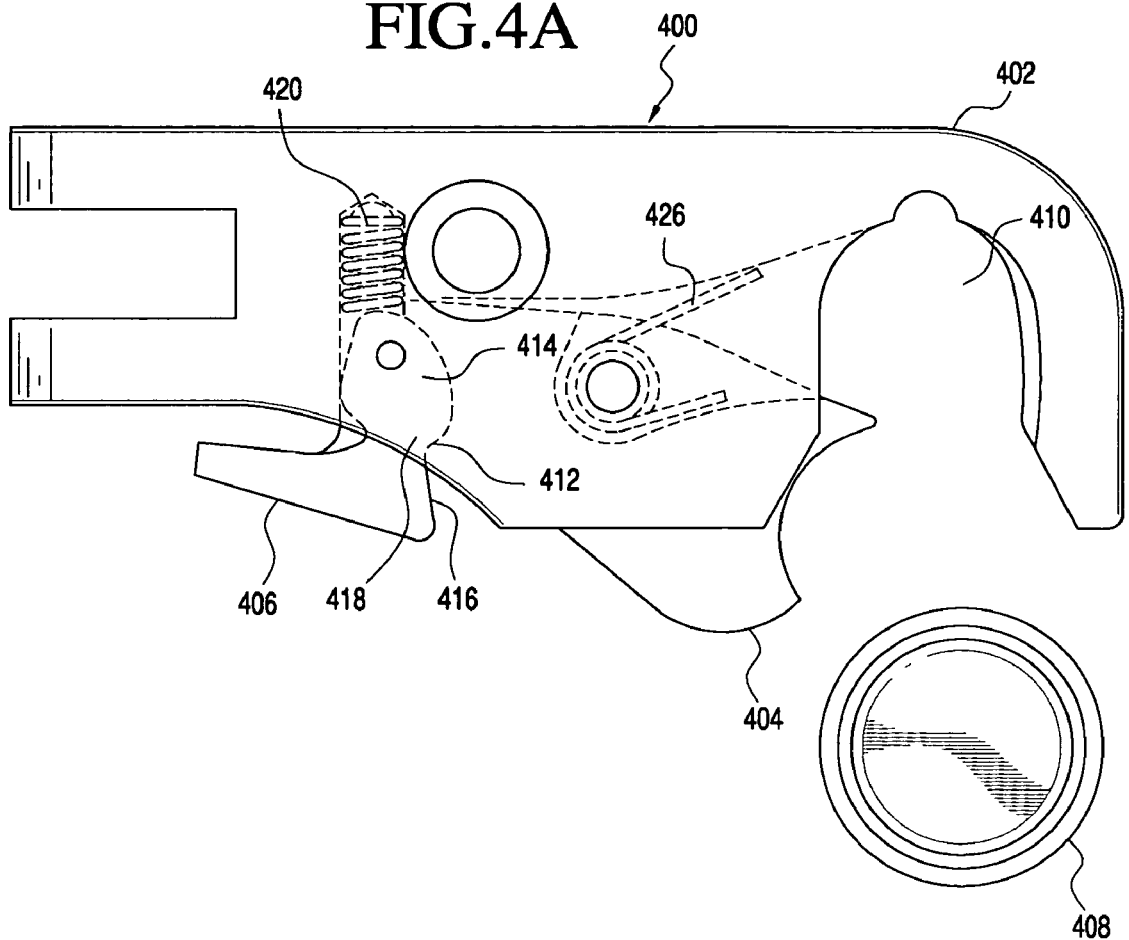
FIGS. 4A and 4B show perspective diagrams of a connector in accordance with another embodiment of the invention.

FIG. 4A shows a perspective view of a connector 400 for a surgical retractor (shown in FIG. 5). The connector 400 includes a body member 402, a retainer 404 and a lock mechanism 406. Also shown in FIG. 4A is a nipple 408 for a retractor blade. The body member 402 includes an opening 410 for receiving the nipple 408 of the retractor blade. The retainer 404 is pivotally mounted to the body member 402 at a pivot point and pivots between an open position and a closed position. A spring 426 biases the retainer 404 in the open position. The distal end 412 of the retainer 404 is in contact with a surface 414 of the locking mechanism (or pawl) 406 while the retainer 404 is in the open position. The pawl (or locking mechanism) 406 is pivotally mounted to the body member 402 between a release position and a lock position. A spring 420 biases the pawl 406 in the lock position. While the retainer 404 is in the open position, the surface 414 of the pawl is in contact with the distal end 412 of the retainer 404.

Figure 4B:
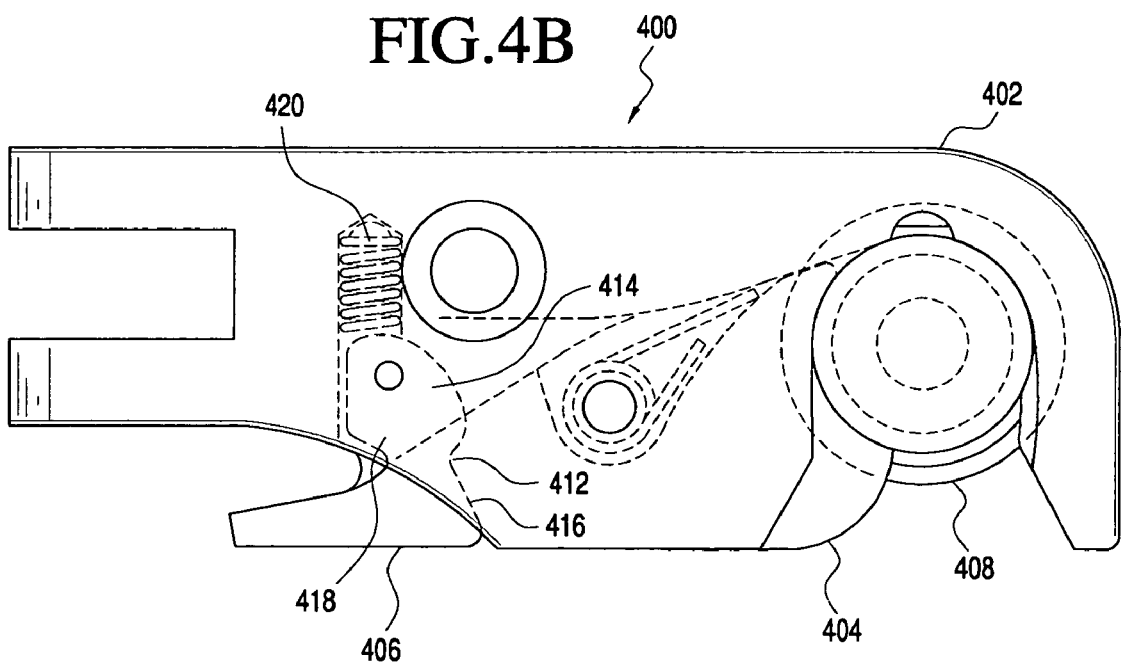

FIG. 4B shows a perspective view of the connector 400 of FIG. 4A with the retainer 404 in the closed position retaining the nipple 408 therein. The spring 420 biases and holds the pawl 406 in the lock position. The distal end 412 of the retainer 406 contacts a surface 416 and is prevented from moving to the open position by a ridge 418. The pawl 406 therefore maintains the retainer 406 in the closed position. If a handle 422 of the pawl 406 is pushed, pivoting the pawl 406 to the release position, the ridge 418 moves away from the distal end 412 of the retainer 404 and allows the retainer 404 to move to the open position from the force of the spring 426.

As with the previously described embodiments, the opening 410 of the body member 402 may be approximately semi-annular in shape and adapted to receive a generally cylindrical nipple. Correspondingly, a mating portion 424 of the retainer may be semi-annular and cylindrical. Alternatively, the opening 410 of the body member 402 may be approximately semi-annular in shape and adapted to receive a tapered nipple. Correspondingly, a mating portion 424 of the retainer is semi-annular and tapered. Although the opening 410 is illustrated as cylindrical or tapered, the opening 410 may have any shape adapted to receive various types of retractor blades having various types of nipples or connector heads.

FIG. 5 shows a perspective view of a surgical retractor assembly 500. The assembly 500 includes a surgical retractor 502, two connectors 504 and two retractor blades 506. The retractor blades 506 include nipples 508 which are retained within the connectors 504 as shown in the embodiments described above.

Figure 6A:
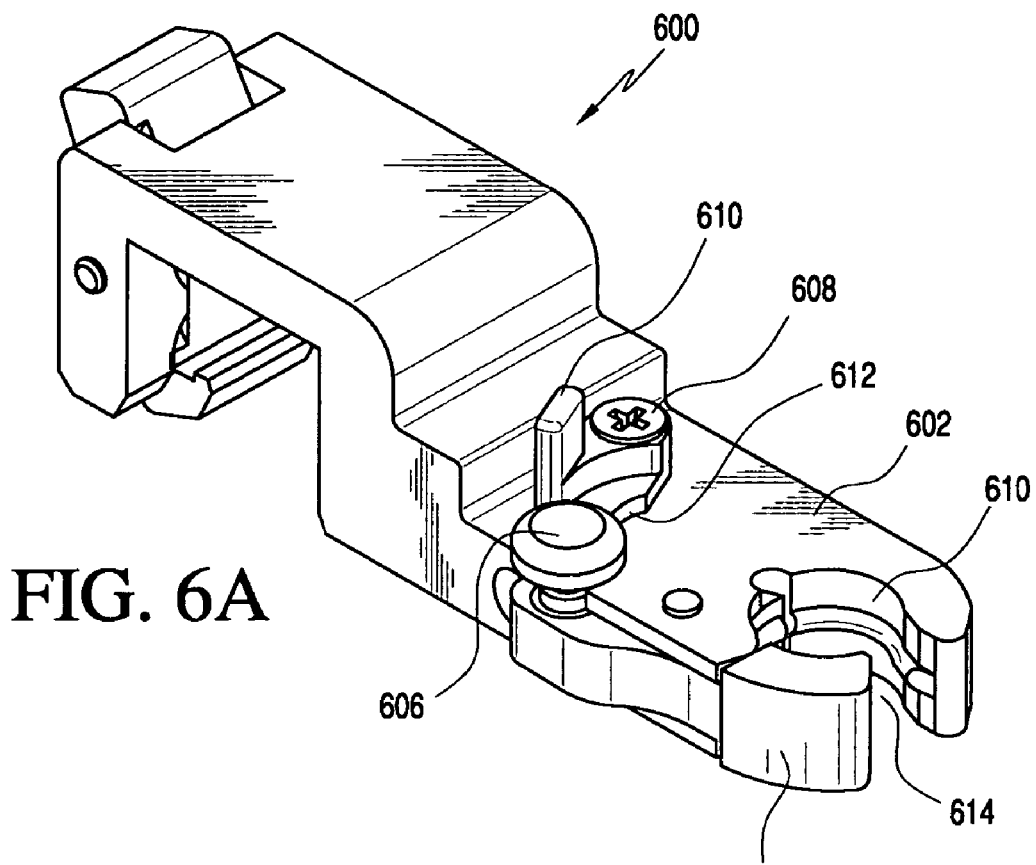
FIGS. 6A and 6B show perspective diagrams of a connector in accordance with another embodiment of the invention.
Figure 6B:
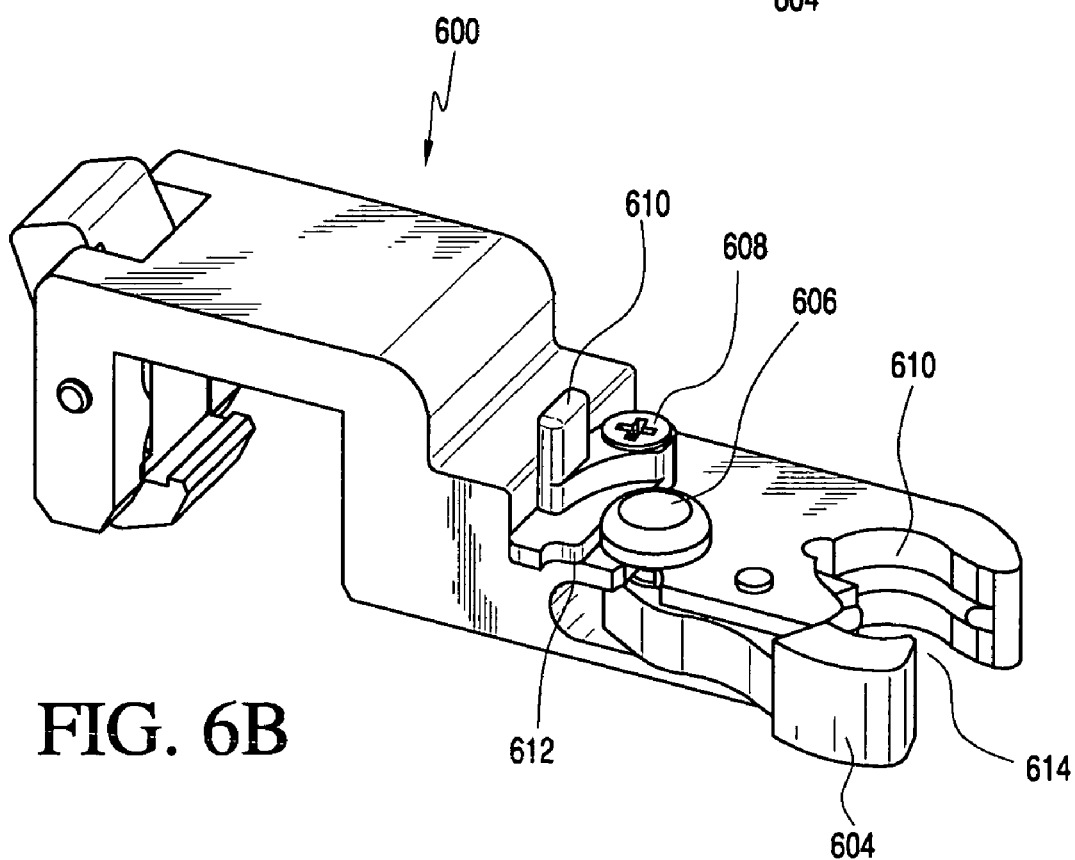
Figure 7:
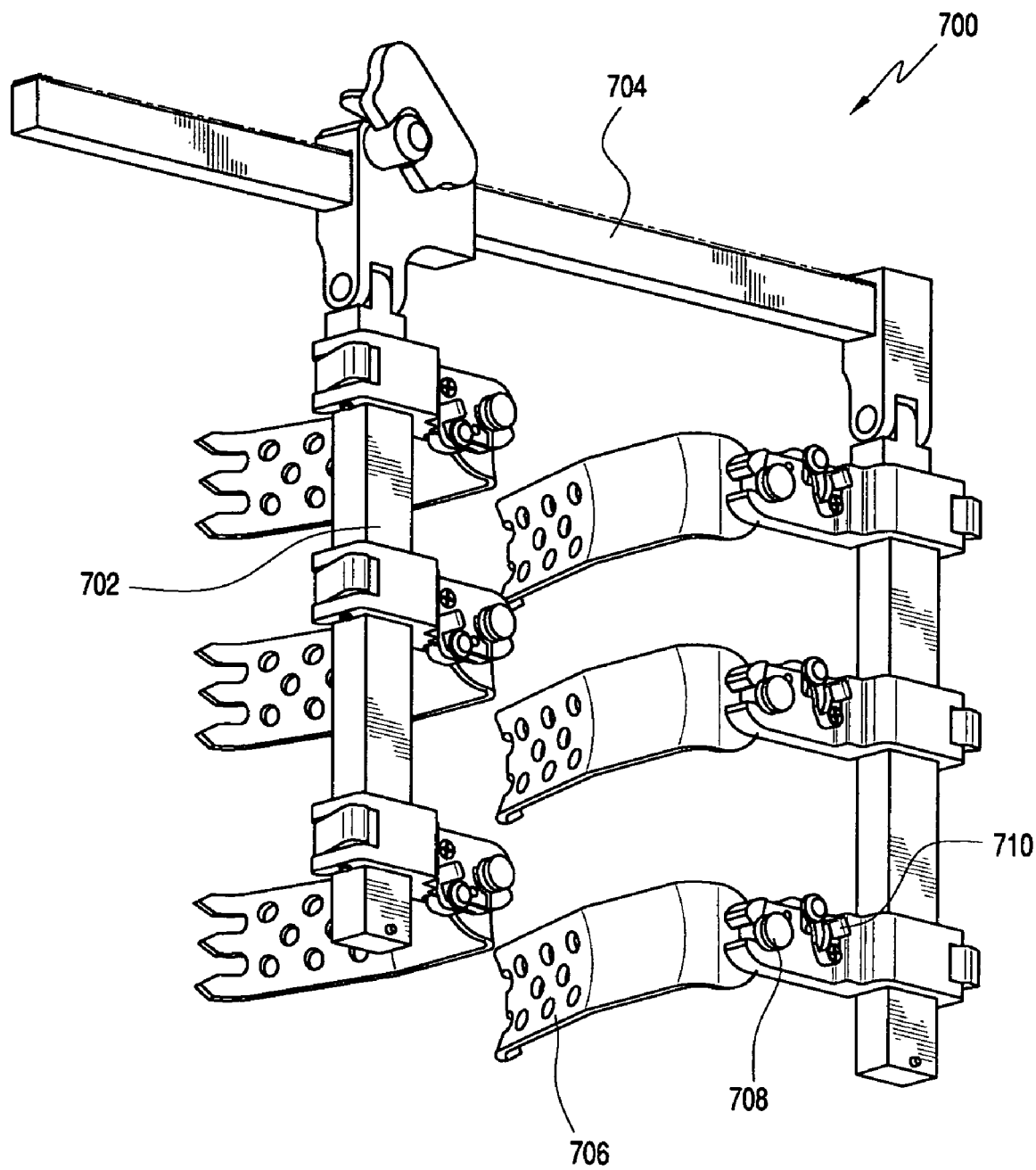
FIG. 7 shows a perspective view of a surgical retractor including connectors in accordance with another embodiment of the invention.

FIGS. 6A and 6B show perspective views of a connector 600 for a surgical retractor (shown in FIG. 7). The connector 600 includes a body member 602, a retainer 604, a lock mechanism 606 and a safety latch 608. The body member 602 includes an opening 610 for receiving a nipple of a retractor blade such as the one described in FIG. 1. However, the opening 610 may be adapted to receive various types of retractor blades having various types of nipples or connector heads. Additionally, the connector 600 is a front loading connecting with the opening 610 located in front of the connector 600 rather than on the side of the connector which is shown in FIGS. 2 and 3. The retainer 604 is pivotally mounted to the body member 602 at a pivot point and pivots between an open position and a closed position.

The connector 600 includes the safety latch 608 which is pivotally mounted to the body member 602. The safety latch 608 includes a grip 610 and a shoulder 612. The grip 610 provides a user with a surface to apply force thus pivoting the safety latch 608. The shoulder 612 engages the lock mechanism 606 between a space and the body 602. This engagement reduces the risk that the user accidentally pushes opens the lock mechanism 606 during use. Once the user attaches a blade to the connector 600, the spring loaded safety latch 608 pivots into place. As shown in FIG. 6A, the locking mechanism 606 is now constrained into position and will not release until the user pivots the safety latch 608 out of position and presses the lock mechanism. The user may apply force to the grip 610 thus pivoting the safety latch 608 from under the lock mechanism 606. Once out of the way, the user may press the lock mechanism 606 to open the retainer 604 as shown in FIG. 6B.

FIG. 7 shows a perspective view of a surgical retractor assembly 700 including front loading connectors as shown in FIG. 6. The assembly 700 includes a surgical retractor arm 602 connected to a second "L" shaped surgical retractor arm 704. The assembly 700 may include a plurality of blades 706 having nipples 708 retained in connectors 710.

What has been described and illustrated herein are examples of the systems and methods described herein along with some of their variations. The terms, descriptions and figures used herein are set forth by way of illustration only and are not meant as limitations. Those skilled in the art will recognize that many variations are possible within the spirit and scope of these examples, which are intended to be defined by the following claims and their equivalents in which all terms are meant in their broadest reasonable sense unless otherwise indicated.

What is claimed is:

1. A connector that retains a surgical retractor, the connector comprising:
   a body member having a top surface and an opening shaped and sized to receive a nipple of a retractor blade;
   a retainer pivotally attached to the body member between an open position and a closed position;
   a lock mechanism, disposed on the retainer, that is shaped to lock the retainer in the closed position, wherein the nipple of the retractor blade is locked in the connector, the lock mechanism comprising a push button including a base at least partially residing within the retainer; and
   a safety latch pivotally mounted to the top surface of the body member that constrains the lock mechanism when the retainer is in the closed position, the safety latch comprising a shoulder that slides into a recess between the push button of the lock mechanism and the top surface of the body member to constrain the lock mechanism in place while the retainer is in the closed position.

2. The connector of claim 1, wherein the opening of the body member is configured to receive a generally cylindrical nipple.

3. The connector of claim 2, wherein the retainer includes a semi-annular, cylindrical mating portion that contacts a surface of the generally cylindrical nipple.

4. The connector of claim 3, wherein the opening of the body includes a raised ridge that aligns with an annular trench located on the cylindrical nipple.

5. The connector of claim 1, wherein the opening of the body member is configured to receive a tapered nipple.

6. The connector of claim 5, wherein the retainer includes a semi-annular, tapered mating portion that contacts a surface of the tapered nipple.

7. A connector that retains a surgical retractor, the connector comprising:
   a body member having a top surface and an opening shaped and sized to receive a nipple of a retractor blade;
   a retainer pivotally attached to the body member between an open position and a closed position;
   a spring that biases the retainer in the open position;
   a lock mechanism, disposed on the retainer, that is shaped to lock the retainer in the closed position, wherein the nipple of the retractor blade is locked in the connector and wherein, when unlocked, the retainer ejects the nipple of the retractor blade from the opening, the lock mechanism comprising a push button including a base at least partially residing within the retainer; and
   a safety latch pivotally mounted to the top surface of the body member that constrains the lock mechanism when the retainer is in the closed position, the safety latch comprising a shoulder that slides into a recess between the push button of the lock mechanism and the top surface of the body member to constrain the lock mechanism in place while the retainer is in the closed position.

8. The connector of claim 7, wherein the opening of the body member is configured to receive a generally cylindrical nipple.

9. The connector of claim 8, wherein the retainer includes a semi-annular, cylindrical mating portion that contacts a surface of the generally cylindrical nipple.

10. The connector of claim 9, wherein the opening of the body includes a raised ridge that aligns with an annular trench located on the cylindrical nipple.

11. The connector of claim 7, wherein the opening of the body member is configured to receive a tapered nipple.

12. The connector of claim 11, wherein the retainer includes a semi-annular, tapered mating portion that contacts a surface of the tapered nipple.

\* \* \* \* \*